US008357918B2

(12) United States Patent
Soh et al.

(10) Patent No.: US 8,357,918 B2
(45) Date of Patent: Jan. 22, 2013

(54) APPARATUS AND METHOD FOR ANALYZING A FLUORESCENT SAMPLE DISPOSED ON A SUBSTRATE

(75) Inventors: Cheong Boon Soh, Singapore (SG); Swee Chuan Tjin, Singapore (SG); Ying Hung Yvonne Lam, Singapore (SG); Lian Soon Ng, Singapore (SG)

(73) Assignee: Nanyang Technological University, Singapore (SG)

( * ) Notice: Subject to any disclaimer, the term of this patent is extended or adjusted under 35 U.S.C. 154(b) by 636 days.

(21) Appl. No.: 12/525,987

(22) PCT Filed: Feb. 5, 2008

(86) PCT No.: PCT/SG2008/000042
§ 371 (c)(1),
(2), (4) Date: Aug. 5, 2009

(87) PCT Pub. No.: WO2008/097199
PCT Pub. Date: Aug. 14, 2008

(65) Prior Publication Data
US 2010/0332150 A1    Dec. 30, 2010

Related U.S. Application Data

(60) Provisional application No. 60/899,657, filed on Feb. 6, 2007.

(51) Int. Cl.
*G01J 1/58* (2006.01)
(52) U.S. Cl. .................. 250/459.1; 250/458.1
(58) Field of Classification Search ........... 250/459.1
See application file for complete search history.

(56) References Cited

U.S. PATENT DOCUMENTS

| 5,270,548 A | 12/1993 | Steinkamp |
| 5,340,715 A * | 8/1994 | Slovacek et al. ........ 435/6.11 |
| 7,154,661 B2 | 12/2006 | Seah et al. |

OTHER PUBLICATIONS

International Search Report for International Application No. PCT/SG2008/000042, Report completed Apr. 16, 2008, 3 pgs.
Written Opinion for International Application No. PCT/SG2008/000042, Opinion completed Apr. 16, 2008, 3 pgs.

* cited by examiner

*Primary Examiner* — Marcus Taningco

(57) ABSTRACT

An apparatus for analysing a fluorescent sample disposed on a substrate comprises a first processor for producing first and second electrical signals derived from respective first and second light signal components received from a sample and from a substrate. The apparatus produces the first and second electrical signals such that there is a phase difference between phases of the first and second electrical signals. The apparatus comprises a control circuit for producing an attenuation signal for attenuating the second electrical signal.

15 Claims, 21 Drawing Sheets

APPARATUS AND METHOD FOR ANALYZING A FLUORESCENT SAMPLE DISPOSED ON A SUBSTRATE

REFERENCE TO RELATED APPLICATION

Reference is made to U.S. provisional patent application No. 60/899,657 filed 6 Feb. 2007 for an invention titled: Elimination of Background Fluorescent Noise Using Interference Cancellation Technique, the contents of which are hereby incorporated by reference as if disclosed herein in their entirety, and the priority of which is hereby claimed.

TECHNICAL FIELD

The invention relates to an apparatus and a method for analysing a fluorescent sample disposed on a substrate.

BACKGROUND

Medical diagnostic tools typically use classical biochemical techniques that involve bulky and expensive equipment such as spectrophotometry, gas chromatography (GC), mass spectrometry (MS), high-performance liquid chromatography (HPLC), paper and thin-layer chromatography (PC and TLC), and electrophoretic techniques coupled with fluorescence detection techniques. These standard analytical tools work effectively and efficiently. However, the tools are expensive and require costly consumables, sample throughput, and experienced and skilled operators. These drawbacks hinder rapid, inexpensive, and in-situ diagnosis of healthcare. Such methods often require tedious and laborious processes. Therefore these tools are mostly used as confirmatory tools for the presumptive positive samples that are initially screened by some kinds of assay techniques.

Quantitative immunoassay techniques pose similar problems. The performance of quantitative immunoassay analysis is largely restricted to centralised laboratories because of the need for long assay times, and for relatively complex, bulky and expensive equipment, as well as highly-trained operators. Thus the analysis is performed far from the patients whose samples are measured. If a wider range of immunoassays could be run in a simpler fashion, more inexpensively and at the point of care or in home health care, the health of large numbers of patients could be improved annually.

Optical biosensors are one of the major types of biosensors to have been exploited for immunoassay applications due to the advantages they can offer, such as improved sensitivity, simplicity and immunity to electromagnetic wave interferences. Many types of optical techniques are commonly used for biosensing applications. Fluorescence-based sensors are perhaps the most highly developed due to their high sensitivity, versatility, accuracy and fairly good selectivity. Fluorescence methods are also very suitable for miniaturisation. The current focus in this area is to measure/detect fluorescently-labelled analytes inside a microfluidic channel by focusing an excitation light source onto a sample inside a microchannel and collecting the fluorescence emission of the sample using a set of complex lenses, mirrors, and optical filters. As a result, a fluorescence signal from the microfluidic substrate may enter the detection system giving rise to a strong but unwanted fluorescence noise. The fluorescence response from the analyte of interest is often rather weak due to the low analyte concentration. As a consequence, fluorescence noise due to the fluorescence of the substrate may suppress the wanted fluorescence signal from the analyte of interest. For early detection of diseases, biomarker concentrations are always low at the early stages of any diseases. Present point-of-care systems have limits in detecting low analyte concentration typical for early detection of diseases.

Two approaches commonly used to mitigate the effects of this are:

1) Incorporation of a confocal fluorescence microscope which can block the signals not from thin layer within which the sample resides. This technique works reasonably well, but it requires bulky, expensive and complicated optics.
2) A material with no or low fluorescence properties is selected as the substrate material. Optical grade glass and silica are commonly used for this purpose, since these materials have low autofluorescence when they are excited by light within visible wavelengths. However, these materials are relatively expensive and fabrication of microfluidic channels using these materials requires time-consuming photomask generation, photolithography and etching processes. As a consequence, the microfluidic chip made from optical grade glass or silica will be relatively expensive.

Candidate inexpensive materials considered as being suitable for use as substrate materials are polymer-based materials, such as polymethyl-methacrylate (PMMA), polycarbonate and Mylar. In addition, microfluidic channels using polymeric materials can be easily fabricated by moulding, embossing, casting or ablation processes. Complex models of microchannels in polymer sheets have been fabricated in less than an hour using a direct-write laser system. However, these materials exhibit relatively high autofluorescence signals which in turn hinder their use for low analyte concentration detection. The intensity of fluorescence background signal from the polymeric materials can be two orders of magnitude higher than fluorescence signal of sample within the microfluidic channel. Hence, utilisation of a polymeric microfluidic chip requires a technique that can resolve and eliminate the auto-fluorescence background noise of polymeric materials.

A background discussion of this technology reveals that when a fluorescent material is excited by a short pulse from an excitation light source, the material will fluoresce in such a way that its intensity decays exponentially with time. The time for the fluorescent intensity of the material to decay to 1/e of the initial intensity at t=0 is called the fluorescent lifetime of the material. In general, due to the chemical composition of the materials, different materials will fluoresce with different lifetimes. In the frequency domain, when the material is excited by a sinusoidally modulated light source, a sinusoidal fluorescence signal will be generated with a frequency that is identical to the frequency of the excitation light source but with its phase shifted with respect to the excitation light. Hence if two fluorescent materials are excited using a sinusoidal light source, two signals will be detected, the phases of which will vary depending on their respective fluorescent lifetimes.

When light, which is modulated to a frequency $f_{mod}$ is incident on the surface of the fluorescently labelled sample inside the microfluidic channel made of polymers, two sets of signals or signal components are produced, assuming that the excitation signal has already been filtered off. These signals/components are (1) the fluorescence signal component emitted by the labelled analyte of interest and (2) the fluorescence background noise signal/component emitted by the substrate. These two sets of signals will have the same modulating frequency as the incident light source, but in general, will be at different phase and amplitude with respect to the incident oscillating light source. This is illustrated in FIG. 1 illustrating the voltage-time characteristics 100 of the two signals, and is due to the difference in the different fluorescence lifetimes of the two polymers. As the analyte of interest immobilised within a microfluidic channel may be very low in concentration, it will form the weaker of the two signals. This weaker signal 102 is denoted as $y_s(t)=A_s \sin(\omega t+\phi_s)$ where $\omega=2\pi f_{mod}$. The stronger signal 104 is the unwanted signal, as it represents the fluorescence background noise from the substrate. This is denoted as $y_n(t)=A_n \sin(\omega t+\phi_n)$. Since, in general, the fluorescence signals from the analyte of interest and the substrate have different fluorescence lifetimes, there exists a phase difference between $y_s(t)$ and $y_n(t)$. The phase difference of the two signals with respect to the incident signal are denoted as $\phi_s$ and $\phi_n$ respectively. Given this, the detection of the weaker fluorescence signal of interest $y_s(t)$, is clearly problematic.

Commonly-assigned International Patent Publication No. WO2007/040459 discloses several techniques in this field. In at least one of these techniques, an output signal from the system which represents the wanted sample fluorescence signal is given by $$\frac{A_s}{2}\sin(\Delta\phi)$$

where $A_s$ is the amplitude of the signal and $\Delta\phi$ is the phase difference between the phase of the wanted sample fluorescence signal and the phase of the unwanted substrate fluorescence signal. An example of this technique is illustrated in circuit 20 of the appended FIG. 2, but a detailed description of the operation of circuit 20 is given in WO2007/040459.

The signal detected by the photodetector III of FIG. 2 is given as $$y_{total}=A_s \sin(\omega t+\phi_s)+A_n \sin(\omega t+\phi_n)$$

To eliminate the noise signal, another signal $q(t)=A_x \cos(\omega t+\phi_n)$ is generated, which is orthogonal to the noise signal component $A_n$, using a phase delay circuit.

Multiplying these two signals, one obtains, $$x_q(t) = y_{total}(t) \times q(t)$$
$$= \frac{A_s A_x}{2}\sin(\phi_s - \phi_n) + \frac{A_s A_x}{2}\sin(2\omega t + \phi_s + \phi_n) + \frac{A_n A_x}{2}\sin(2\omega t + 2\phi_n)$$

$$\frac{A_s A_x}{2}\sin(2\omega t + \phi_s + \phi_n) \text{ and } \frac{A_n A_x}{2}\sin(2\omega t + 2\phi_n)$$

are eliminated by the low pass filter leaving $$\frac{A_s A_x}{2}\sin(\phi_s + \phi_n),$$

which is a DC signal that is dependent on the phase difference $\phi_s - \phi_n$.

$$\frac{A_s A_x}{2}\sin(\phi_s + \phi_n)$$

is maximum when $\phi_s - \phi_n$ is 90°.

The phase difference is dependent on fluorescence lifetimes between the signal $A_s$ and the noise $A_n$ as well as the modulation frequency of the excitation light source I. As an example, for fluorescein and mylar, the fluorescent lifetime difference is 1 ns and to generate a 90° phase difference, the modulation frequency required for light source I is 250 MHz. Such high frequencies can be achieved using laser diodes but not LEDs. The dependence of the phase difference on the modulating frequency is not in direct proportion. In general, it is not possible to obtain a 90° phase shift. Depending on the samples, there will be a certain frequency at which the phase difference is a maximum. That will be the optimal operating frequency for that system. The shorter the difference in lifetimes, the higher is this frequency.

The DC output obtained by circuit 20 is $$\frac{A_s A_x}{2}.$$

SUMMARY

The invention is defined in the independent claims. Some optional features of the invention are defined in the dependent claims.

By providing an apparatus for analysing the fluorescent sample disposed upon a substrate with a control circuit to produce an attenuation signal for attenuating the noise signal component several benefits are realised.

A DC output given by $A_s$ may be obtained even if the phase difference between the first (wanted) and second (noise) signals is much less than 90°. Thus, an apparatus for analysing the fluorescent sample is able to recover the full amplitude, $A_s$, of the signal even when the phase difference between the sample signal and the background signal is not at 90°. This implies that the light source need not be modulated at very high frequency as presently required. Currently, the maximum modulating frequency for an LED is approximately 10 MHz. Using this frequency and taking, as an example, the fluorescent lifetime difference to be 1 ns, the phase difference between the two fluorescent signals is calculated to be $\Delta\phi=3.6°$. In WO2007/040459, the output signal from the circuit is defined by $$\frac{\sin(3.6°)}{2} = 0.0314,$$

the equivalent of 30 dB attenuation (for example, 7.9 mV output compared to 250 mV). Additionally, a phase difference of 90° between the wanted and unwanted signals is needed to maximise the output signal from WO2007/040459 which is half of the output signal given by an apparatus in accordance with claim 1, which does not require such a phase difference. Using the 1 ns lifetime difference, the light source of WO2007/040459 has to be modulated at 250 MHz, a modulation frequency which can only be achieved using laser diodes. Although it is still a viable technique, the overall cost of implementation is therefore higher than the present technique which may recover the signal of interest even if the phase difference is much less than 90°, thus allowing the less expensive LED to be used.

As such there is no need to locate the optimal operating frequency but to operate at a frequency to provide a phase difference of 1° or 2°. Therefore, there is no need to have a very high modulating frequency.

BRIEF DESCRIPTION OF THE DRAWINGS

The invention will now be described, by way of example only, and with reference to the following drawings in which.

DETAILED DESCRIPTION OF PREFERRED EMBODIMENTS

Figure 1:
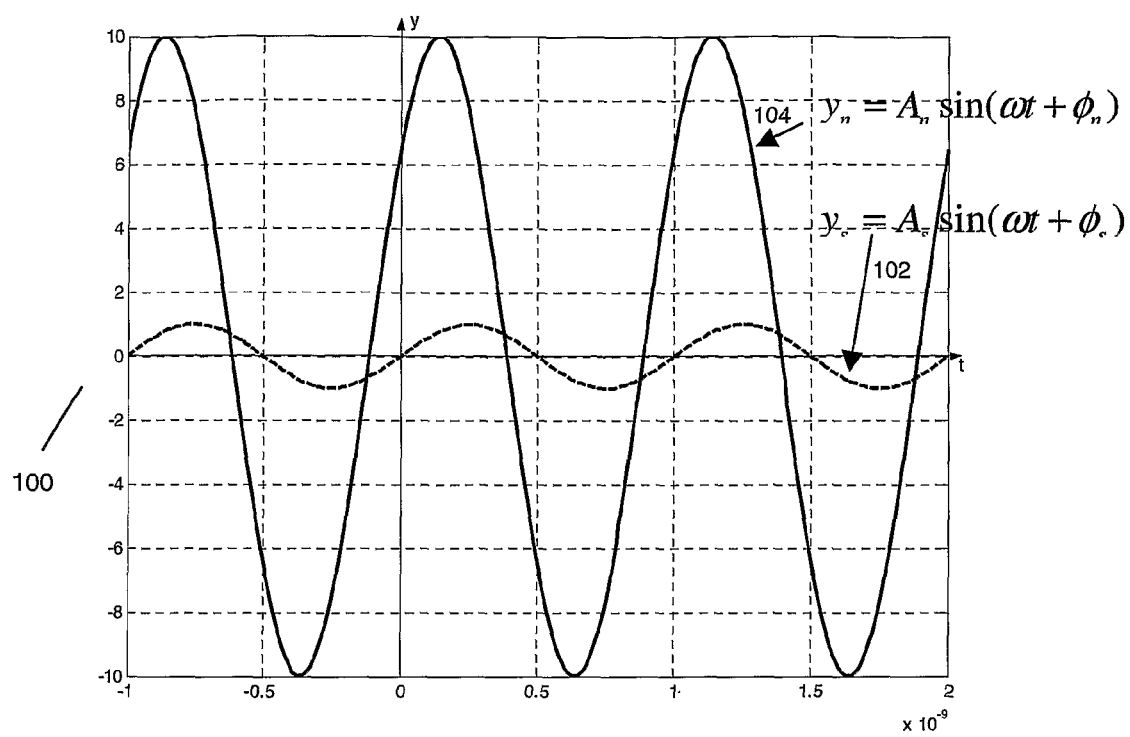
FIG. 1 is a graph illustrating voltage-time curves of typical wanted and unwanted signal components.
Figure 2:
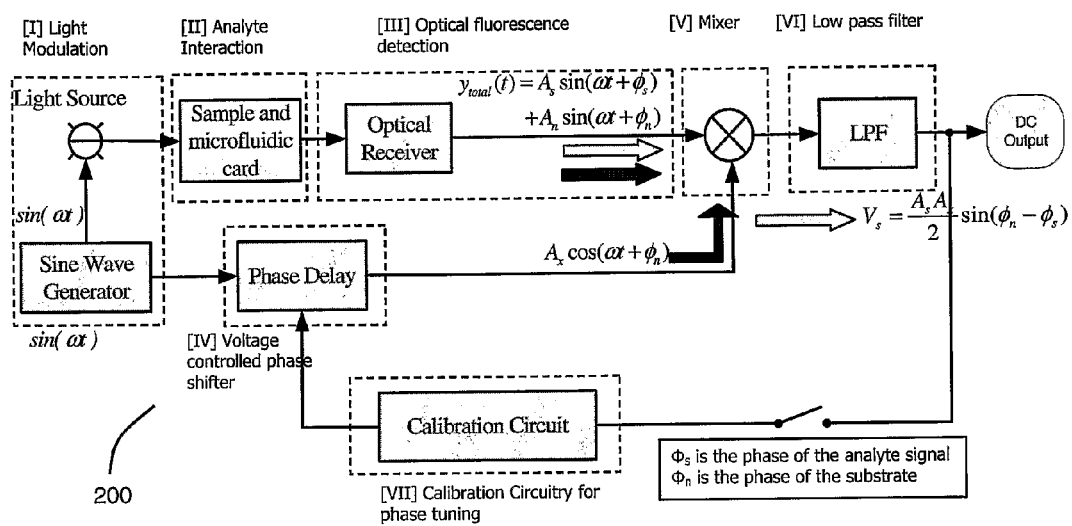
FIG. 2 is a block diagram illustrating a known circuit architecture for analysing a fluorescent sample disposed on a substrate.
Figure 3:
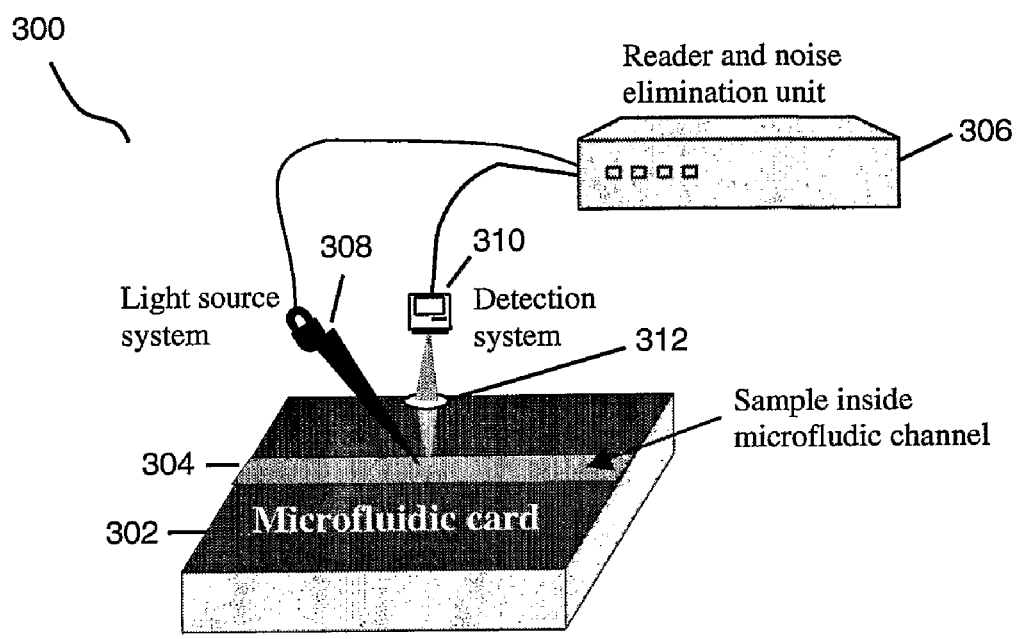
FIG. 3 is a schematic diagram of a geometrical configuration of an apparatus for analysing a fluorescent sample disposed on a substrate.

Referring to FIG. 3, a geometric arrangement of an apparatus for analysing a fluorescent sample disposed on a substrate is illustrated. The apparatus 300 comprises a microfluidic card 302 with a fluorescent sample 304 disposed inside a microfluidic channel on the microfluidic card substrate 302. A reader and noise elimination unit 306 is arranged to provide light via light source system 308 to excite the fluorescent sample 304. Detection system 301 receives light from the fluorescent sample 304 and reflections/noise from microfluidic card substrate 302 for transmission to and processing by reader and noise elimination unit 306.

Because microfluidic channels based on polycarbonate materials, such as PMMA and Mylar, are relatively cheap and can be fabricated easily, polycarbonate materials became an important material for a microfluidic applications, which are often considered a consumable item. However, the fluorescence background of polycarbonate materials is considerably high, particularly compared to the fluorescence intensity of the analyte of interest immobilised inside a microfluidic channel. The compact and simple fluorescence detection system 300 of FIG. 3, will pick up not only fluorescence emission of analyte of interest 304, but also other light emissions generated at the illuminated spot, such as fluorescence from microfluidic substrate 302.

Different types of light sources can be used as the excitation light source 308. Examples are lasers of appropriate wavelength including laser diodes, LEDs and broadband light sources. The wavelength of the light source 308 has to be such that it can excite the fluorophore label attached to the analyte. For an example, if the fluorophore label is fluorescein, a light source with wavelength between 450 nm and 500 nm is required. The wavelength of light source 308 may only have a single wavelength, i.e. light emitted by a laser or laser diode. However, a laser source is usually relatively bulky and expensive. In addition, a laser and laser diode are only available at certain wavelengths which may not be suitable for a broad range of different types of fluorophores. If the light source 308 used is an LED which may cover not only the excitation wavelength region, but also fluorescence wavelength region, a suitable low-pass optical filter or band-pass optical filter (not shown), can be installed between the LED 308 and the microfluidic card 302. The light beam, particularly from an LED 308, diverges, so that a focusing lens system may be provided to focus the light into the sample 304 inside a microchannel.

The intensity of fluorescence emissions from the labeled analyte 302 and the substrate 304 is proportional to the intensity of light from the excitation light source 308. However, if the intensity of the light source 308 is too high, it may cause quick photodestruction or photobleaching of the fluorophore. The inventors have found that a 470 nm blue LED with 3460 mcd in intensity is a suitable light source to excite fluorescein.

The light source 308 is modulated at such a frequency such that there exists a phase difference between the fluorescence signal of interest and the unwanted, noise signal. The modulation frequency to achieve this condition depends on the difference between the fluorescence lifetimes of the fluorophore labeled analyte 304 and the microfluidic substrate 302. The modulation frequency can be calculated using equation (1) as follows:

$$f_{mod} = \frac{1}{4(\Delta t)} \quad (1)$$

where $\Delta t$ is the fluorescence lifetime difference between the labeled analyte 304 and the substrate 302.

As an example, if Δt=1 ns, then $f_{mod}$=250 MHz. It is found that in general, an LED can be modulated up to 10 MHz only. Therefore, if a high frequency modulation is required, a laser source or laser diode may have to be used.

As noted above, the light source 308 may have its excitation frequency modulated to ensure that there is a phase difference between the phases of the wanted and unwanted signals. Alternatively, the phase difference could be generated in the reader and noise elimination unit 306 in either optical receiver detection system 310 or in processing electronics in unit 306. A significant aspect of the techniques disclosed herein is that the electrical signals or signal components representing the respective light signals from the sample and from the substrate have a phase difference between them.

The working region of the optical detector 310 must cover the fluorescence wavelength of the analyte 304 of interest. For instance, if the fluorophore used is fluorescein that has fluorescence wavelength range between 500 nm and 600 nm, the optical detector 310 must be sensitive to this wavelength range. An optical filter 310, either a long-pass filter or a band-pass filter, may need to be installed in front of the receiver/detector 310, to filter off signals with wavelengths outside the range of interest. As the light source 308 in system 300 is modulated at a certain modulation frequency, the optical receiver 310 must also be able to respond to the modulated signals at that frequency. There are many types of optical receivers/detectors suitable for this method including photodiodes, avalanche photodiodes, and photomultiplier tubes. A photomultiplier tube is a very sensitive light detector, but the size is relatively bulky, and requires high biasing voltage (1000V). On the other hand, a photodiode is cheap, compact, and simple, but its sensitivity is not as good as a photomultiplier tube and may not be suitable for very weak fluorescence signal. As a compromise an avalanche photodiode is relatively inexpensive, compact, and has good sensitivity. For multichannel detection systems, an array CCD detector offers a good option.

Figure 4:
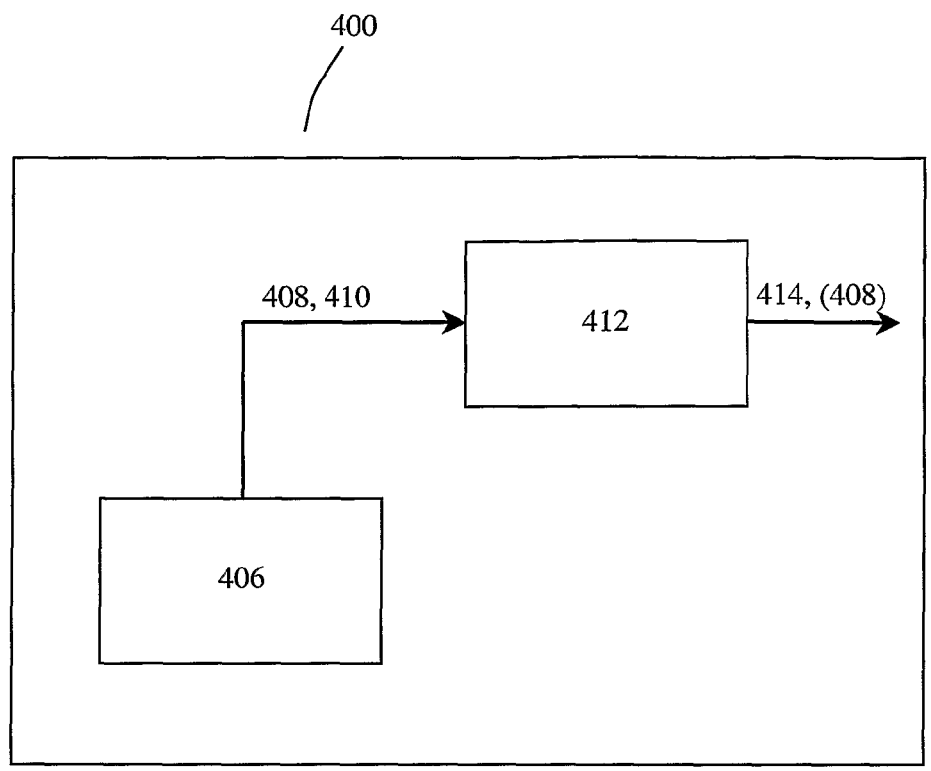
FIG. 4 is a block diagram illustrating an architecture of an apparatus for analysing a fluorescent sample disposed on a substrate.
Figure 4:
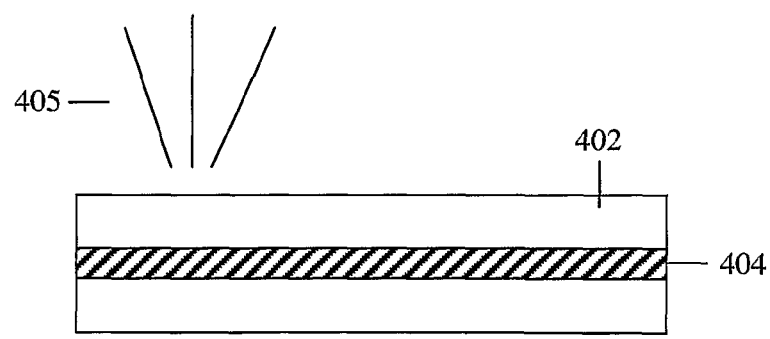

Referring now to FIG. 4, a second apparatus for analysing a fluorescent sample disposed on a substrate is now discussed. The apparatus 400 is arranged to analyse the sample 404 disposed on substrate 402. Light 405 is emitted from the analyte 404 and the substrate 402 to be processed by apparatus 400.

Apparatus 400 comprises first processor 406. First processor 406 may be configured either to receive electrical signals from an optical reader (not shown) for receiving the light signal(s) 405 or the optical reader may be integral with first processor 406.

First processor 406 receives the light signals 405 which includes both the first light signal component from the sample 404 and the second light component from the substrate 402. The light transmitted from the substrate 402 and sample 404 may comprise either fluorescent light emitted from the excited fluorescent sample 404 and/or light directly reflected from a light source (not shown) which excites the sample and substrate. First processor 406 produces a first electrical signal 408 derived from the first light signal component from the sample 404 and a second electrical signal 410 derived from a second light signal component from the substrate 402. The first signal 408 and second signal 410 are supplied to control circuit 412 which produces an attenuation signal for attenuating the second electrical signal 410. The output signal 414 of control circuit 412. When control circuit 412 attenuates the second electrical signal 412 sufficiently or completely, output signal 412 effectively comprises first electrical signal 408. Thus, control circuit 412 cancels or at least substantially cancels the second electrical signal 410 representing the background light noise from the substrate 404.

Figure 5:
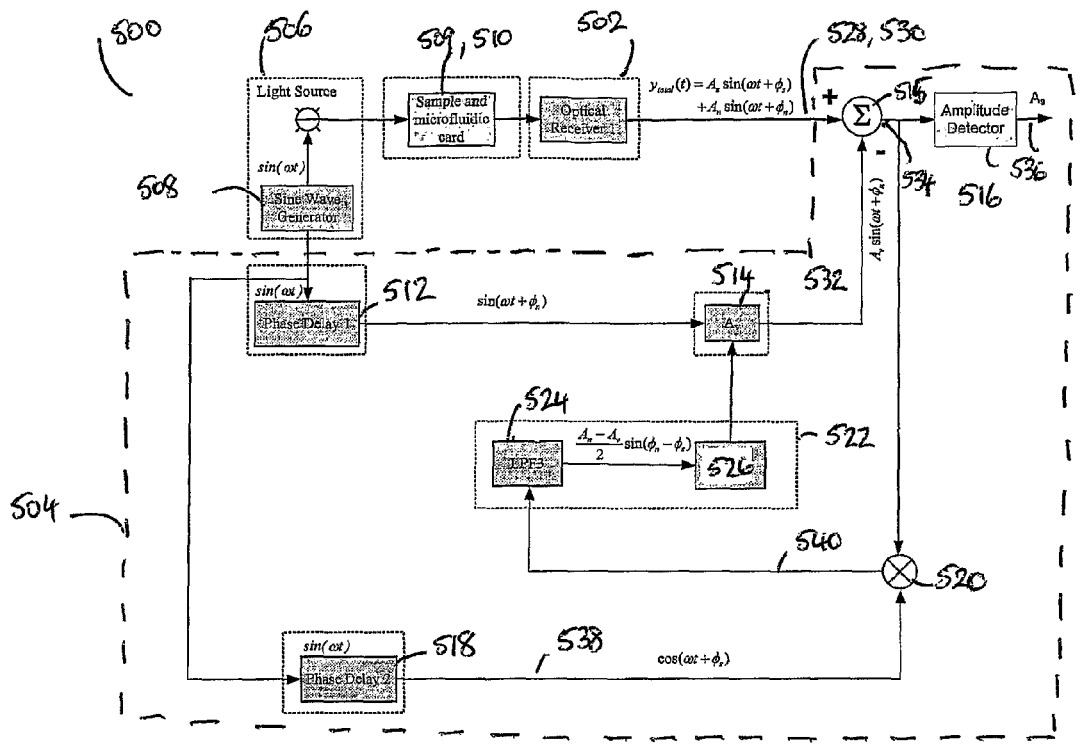
FIG. 5 is a block diagram illustrating a circuit architecture for a second apparatus for analysing a fluorescent sample disposed on a substrate.

Turning to FIG. 5, another apparatus 500 for analysing a fluorescent sample disposed on a substrate is now described. Circuit 500 comprises first processor 502 which in the present example is optical receiver 1. As noted above, the optical receiver may actually be provided separately or integral with the processing electronics for processing the received light signals from the sample 509 and microfluidic card 510. In the example of FIG. 5, the first processor 502 is an integral optical receiver and signal processing unit which receives the light signals and processes these to produce the first electrical signal 528 derived from the first light signal component from the sample 509 and the second electrical signal 530 derived from the second light signal component from the microfluidic card substrate 510.

Additionally, the apparatus comprises control circuit 504 for producing an attenuation signal 532 for attenuating the second electrical signal 530.

The circuit architecture 500 and operation will now be described. As noted above, first processor (optical receiver 1) 502 receives the light signals from the sample 509 and microfluidic card 510. The signals 528, 530 derived by first processor 502 are supplied to summer module 515. Light source 506 is excited by sine wave generator 508. In turn, sine wave generator 508 also excites first phase generator 512 (phase delay 1), the output of which is supplied to variable gain module 514. The output of variable gain module 514 is signal 532 which comprises the attenuation signal. Sine wave generator 508 also excites second phase generator 518 (phase delay 2), the output of which is connected to first mixer 520. The output 534 of summer module 515 is also supplied to first mixer 520. The output of mixer 520 is supplied as an input to circuit 522. Circuit 522 comprises a filter 524 (LPF3) and control circuit 526 for controlling the variable gain module 514.

A detailed mathematical analysis of the operation of circuit 500 is given below. Prior to this, the operation is summarised as follows.

First phase generator 512 is arranged to set a phase of the attenuation signal 532 and the variable gain module 514 is arranged to set an amplitude of the attenuation signal 532. The control circuit 504 is arranged for the attenuation signal to cancel or cancel substantially the second electrical signal component 530. To do this, first phase generator 512 sets the phase of the attenuation signal to be equal or substantially equal to the phase of the second electrical signal 530. This is illustrated in FIG. 5 where it shows the output of first phase generator 512 is of the form $\sin(\omega t+\phi_n)$.

To set (or tune) the amplitude of the attenuation signal 532, variable gain module 514 sets the amplitude to be equal or substantially equal of the second electrical signal 530.

Attenuation of the second electrical signal 530 is effected by supplying the output 528, 530 of first processor 502 to summer module 515 where the attenuation signal 532 is subtracted from signal 528, 530. When attenuation signal 532 is the same, or substantially the same, as unwanted signal 530, unwanted signal 530 is cancelled from the output of summer module 515.

Control circuit 504 feeds back an output 534 of summer module 515 is fed back to mixer 520 for control of the variable gain module 514. An output 538 of second phase generator 518 (phase delay 2) is also fed to mixer 520. The output 540 of mixer 520 is a first mixed signal to control the variable gain module 514. This is supplied to filter 524 and control circuit 526.

Second phase generator 518 sets its output signal 538 to have a phase equal to or substantially equal to a phase of first electrical signal 528. That is, the phase is set substantially to the phase of the wanted signal received at first processor 502 from sample 509.

Alternatively, all of the components illustrated may be provided in a single apparatus 500 comprising a tuneable modulated light source 506 for exciting the fluorescent sample 509; optical receiver 502 for receiving light signal components from the fluorescent sample 509 and from the substrate 510; a first phase delay generator 512 and variable gain module 514; a second phase delay generator 518 and a control circuit 522 for the variable gain module 514.

The mathematical analysis of the circuit 500 operation is now given. Firstly, the frequency $\omega t$ of light source 506 excitation 508 is tuned so that there is a phase difference between signal of interest 528 $y_s$ generated by the sample 509 and unwanted signal 530 $y_n$ generated by the microfluidic card 510.

The signal 534 $y_{sum}$ after the summer 515 is composed of the signal 528 $y_s$ generated by the sample 509, unwanted signal 530 $y_n$ generated by the microfluidic system 510 and the generated attenuation signal 532 $-A_v \sin(\omega t + \phi_n)$ as follows:

$$y_{sum} = y_s + y_n - A_v \sin(\omega t + \phi_n) \quad (2)$$
$$= A_s \sin(\omega t + \phi_s) + A_n \sin(\omega t + \phi_n) - A_v \sin(\omega t + \phi_n)$$
$$= A_s \sin(\omega t + \phi_s) + (A_n - A_v) \sin(\omega t + \phi_n)$$

The output $q_2(t)$ 538 of the second phase generator 518 is given by:

$$q_2(t) = \cos(\omega t + \phi_s) \quad (3)$$

Mixing in first mixer 520 of signal 534 defined by equation (2) and signal 538 defined by equation (3) results in first mixed signal 540 defined by:

$$x_{q_2}(t) = y_{sum}(t) \times q_2(t) \quad (4)$$
$$= [A_s \sin(\omega t + \phi_s) + (A_n - A_v) \sin(\omega t + \phi_n)] \times \cos(\omega t + \phi_s)$$
$$= A_s \sin(\omega t + \phi_s) \cos(\omega t + \phi_s) +$$
$$(A_n - A_v) \sin(\omega t + \phi_n) \cos(\omega t + \phi_s)$$
$$= \frac{A_s}{2} \sin(2\omega t + 2\phi_s) + \frac{(A_n - A_v)}{2} \sin(2\omega t + \phi_n + \phi_s) +$$
$$\frac{(A_n - A_v)}{2} \sin(\phi_n - \phi_s)$$

Thus, it is seen that first mixed signal 540 comprises a DC component and an AC components in Equation (4). Suppose the AC components are filtered off using a low pass filter 524 (LPF3), only the DC component which is the error signal $V_e$ is left given by $$V_e = \frac{(A_n - A_v)}{2} \sin(\phi_n - \phi_s) \quad (5)$$

The error signal $V_e$ is fed into the control circuit 526 to adjust the gain $A_v$ of the gain module 514 to control the amplitude of the generated signal 512 to cancel the unwanted substrate fluorescence signal 530, $y_n$. The control circuit 526 is a standard control circuit to map the error voltage to the variable gain amplifier 514. This is achieved when $$V_e = 0 \text{ and } A_v = A_n$$

Using (2), the output 534 of the summer module 515 $y_{sum} = y_s$.

The amplitude 536 $A_s$ of the wanted sample fluorescence signal 528 $y_s$ is output by an amplitude detector 536.

The technique is also applicable when the output of the first processor 502 (optical receiver 1) from the unwanted substrate fluorescence signal 530, $y_n(t)$ is given by $$y_n(t) = A_0 + A_n \sin(\omega t + \phi_n) + \sum_{k=2}^{\infty} \alpha_k \sin(k\omega t + \phi_k) \quad (6)$$

The coefficients $\alpha_k$ and the phases $\phi_k$ for $k = 2, \ldots, \infty$ of the signal 530 $y_n(t)$ can be unknown because mixing (3) with components of signal 530 $y_n(t)$ in (6) results in $$\alpha_k \sin(k\omega t + \phi_k) \cos(\omega t + \phi_s) = \quad (7)$$
$$\frac{\alpha_k}{2} [\sin((k+1)\omega t + \phi_k + \phi_s) + \sin((k-1)\omega t + \phi_k - \phi_s)]$$

The resultant signal in (7) and $A_0 \cos(\omega t + \phi_s)$ can be filtered out using the same low pass filter 524 (LPF3). Therefore the error signal to the control circuit 536 is the same as given by $V_e$, in (5). Hence the output of the summer 515 after a band-pass filter to reject the DC component $A_0$ and the higher order harmonics ($k \geq 2$) with $V_e = 0$ will be the wanted sample fluorescence signal 528 $y_s$. The amplitude 539 $A_s$ of the wanted sample fluorescence signal 528 $y_s$ can be measured using the amplitude detector 516 after the band-pass filter (not shown in FIG. 5).

A performance assessment of circuit 500 shows that the interference cancellation technique implemented is able to recover the wanted sample fluorescence signal for a phase difference of 1.08 degrees corresponding to a modulation frequency of 3 MHz. Thus, this enables low-cost implementation using LEDs as this is desired modulation frequency is well within the range of modulation having a maximum modulation frequency of approximately 10 MHz.

Figure 6:
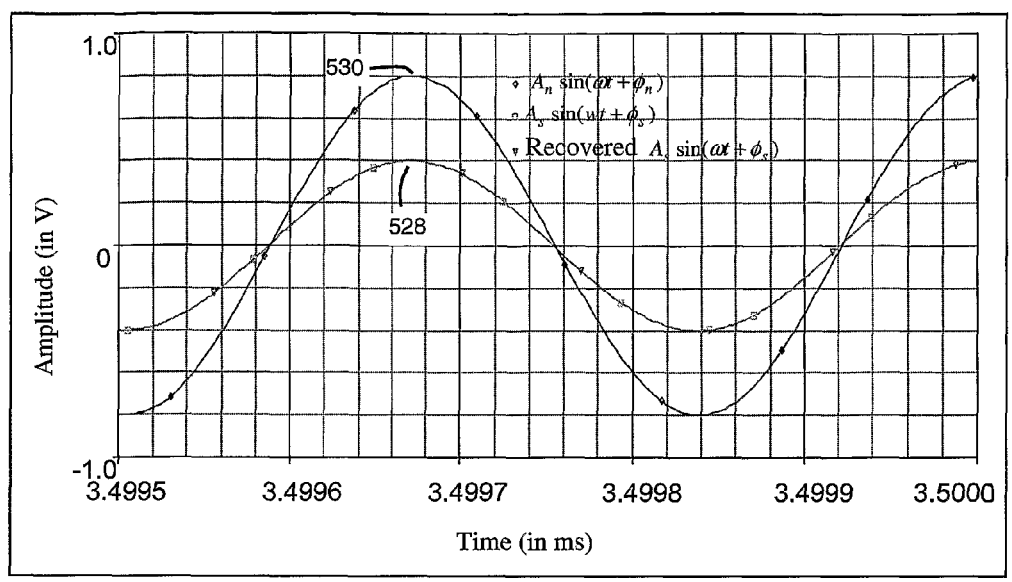
FIG. 6 is a graph illustrating the voltage-time curves of the wanted and unwanted signal components for the circuit of FIG. 5.

With the frequency of modulation set to 3 MHz, this gives a phase difference of 1.08 degrees. The amplitude of the wanted sample fluorescence signal 528 is $A_s = 0.4$ V and the unwanted substrate fluorescence signal 530 is $A_n = 0.8$ V. FIG. 6 shows that the wanted sample fluorescence signal 528 can be recovered in its entirety without loss, thereby providing a significant improvement over known techniques.

Thus, a significant advantage of this technique is that it is able to discriminate very weak fluorescence signals from analytes of interest inside microfluidic chips from much larger unwanted fluorescence signals due to fluorescence background of microfluidic substrate. This is achievable even at low modulation frequencies such that the phase difference between the substrate signal and the analyte signal may be much less than 90°. Hence, the technique makes the detection of very low concentration of analyte inside the microfluidic chip, made from materials with high fluorescence properties, possible.

Because this technique enables elimination of the noise signal due to the fluorescence background of microfluidic substrate, high background fluorescence of the polymeric materials can be used for the microfluidic substrate. Utilising polymeric sheets as the microfluidic material provides many benefits, including low cost, ease of fabrication and robustness. Polymeric sheets tend to be cheaper than optical grade glasses and silica wafers, commonly used now as the microfluidic substrate. Hence the cost of the microfluidic chips can be significantly reduced, possibly allowing them even to be treated as consumable and disposable cartridges in a point-of-care immunoassay system. Polymeric microfluidic chips are robust, so they are also suitable for less-skilled/laboratory assistants.

Figure 7:
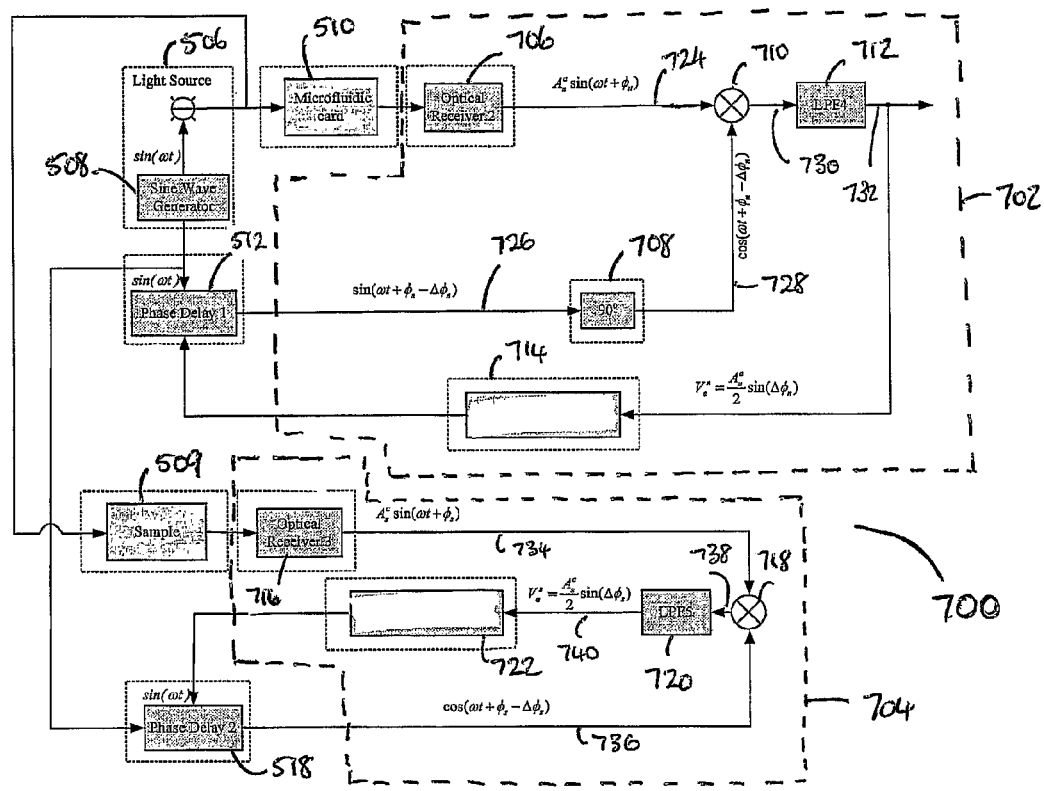
FIG. 7 is a block diagram illustrating an architecture for a calibration circuit for the circuit of FIG. 5.

Prior to use, the circuit for FIG. 5 may first be calibrated. Referring to FIG. 7, a calibration technique is now described with reference to circuit 700.

Circuit 700 comprises a first calibration circuit 702 for calibrating the first phase generator 512 and a second calibration circuit 704 for calibrating the second phase generator 518.

First calibration circuit 702 comprises a second processor 706 (optical receiver 2) for producing a third electrical signal 724 derived from the second light signal component from the substrate 510. The apparatus 700 is arranged to produce third electrical signal 724 without the third electrical signal containing a component derived from the first light signal component. As described below, this is effected by removing the sample from the microfluidic card and exposing the microfluidic card 510 to light from light source 506.

First calibration circuit 702 further comprises a quadrature phase shifter 708 to shift a phase of an output signal 726 from the first phase generator 512. The output of quadrature phase shifter 708 is a shifted signal 728 which is fed to second mixer 710 for mixing with the third electrical signal 724 to produce a second mixed signal 730. Second mixed signal 730 is supplied as an input to first calibration filter 712 (LPF4). A mathematical analysis for this operation is given below. The output signal 732 of first calibration filter 712 is fed back as a control input to control module 714, which, therefore, provides a control input of the first calibration circuit.

The second calibration circuit 704 of apparatus 700 is for calibrating the second phase generator 518. Second calibration circuit 704 comprises a third processor 716 (optical receiver 3) which produces a fourth electrical signal 734 derived from the first light signal component from the substrate. First processor 716 produces the fourth electrical signal without the fourth electrical signal 734 containing a component derived from the second light signal component. This is effected by receiving at third processor 716 light from the sample 509 without any background/noise light from substrate 510.

The fourth electrical signal 734 is supplied to third mixer 718 for mixing with an output 736 of second phase delay generator 518. The output 738 of third mixer 718 is a third mixed signal which is supplied to a second calibration filter 720 (LPF5), the output 740 of which is fed back as a control input of the second calibration circuit 704 to stage 722. The mathematical analysis of this provided below.

The main circuit 500 is first disconnected from the overall system for the calibration stage to tune the phase generators 512, 518. This involves the tuning of first phase generator 512 to $\phi_n$, where $\phi_n$ is the phase of the unwanted substrate fluorescence signal 530 and a microfluidic card 510 without sample 509 being inserted into the calibration system 700 to tune the first phase generator 512 to $\phi_n$. At the same time, second phase generator 518 is tuned to generate the required annihilator signal $\cos(\omega t+\phi_s)$ 538, where $\phi_s$ is the phase of the wanted sample fluorescence signal 528 and a sample 509 without microfluidic card 510 being inserted into the calibration system 700 to tune the second phase generator 518 to generate $\cos(\omega t+\phi_s)$.

The tuning of the first phase generator 512 to set a phase of the attenuation signal equal (or substantially equal) to the phase of unwanted second signal 530 is now described.

The signal 724 $y_n^c(t)$ after the second processor 706 (optical receiver 2) is as follows $$y_n^c(t) = A_n^c \sin(\omega t + \phi_n) \tag{8}$$

The generated signal 726 $y_1^g(t)$ of the first phase generator 512 is given by $$y_1^g(t) = \sin(\omega t + \phi_n - \Delta\phi_n) \tag{9}$$

It follows that the shifted signal 728 $q_1^c(t)$ after the quadrature phase shifter 708 is given by $$q_1^c(t) = \cos(\omega t + \phi_n - \Delta\phi_n) \tag{10}$$

Mixing in second mixer 710 of signal 724 (equation (8)) and signal 728 (equation (10)) results in second mixed signal 730 defined by:

$$\begin{aligned} x_{q_1^c}(t) &= y_n^c(t) \times q_1^c(t) \\ &= A_n^c \sin(\omega t + \phi_n) \times \cos(\omega t + \phi_n - \Delta\phi_n) \\ &= \frac{A_n^c}{2} \sin(2\omega t + 2\phi_n - \Delta\phi_n) + \frac{A_n^c}{2} \sin(\Delta\phi_n) \end{aligned} \tag{11}$$

It can be seen there is a DC component and an AC component in (11). Suppose the AC component is filtered off using a first calibration filter 712 (e.g. low pass filter LPF4), only the DC component which is the error signal $V_3''$ is left signal 732 given by $$V_e^n = \frac{A_n^c}{2} \sin(\Delta\phi_n) \tag{12}$$

The error signal 732 $V_e^n$ is fed into the control circuit 714 to adjust the first phase generator 512 until $V_e^n=0$ and the first phase generator 512 is tuned to $\phi_n$, where $\phi_n$ is the phase of the unwanted substrate fluorescence signal 530.

The tuning of the second phase generator 518 to set this to (or substantially to) the phase of the wanted sample fluorescence signal 528 is now described.

The signal 734 $y_s^c(t)$ after the third processor 716 (optical receiver 3) is as follows $$y_s^c(t) = A_s^c \sin(\omega t + \phi_s) \tag{13}$$

The generated signal 736 $y_2^g(t)$ of the second phase generator 518 is given by $$y_2^g(t) = q_2^c(t) = \cos(\omega t + \phi_s - \Delta\phi_s) \tag{14}$$

Mixing in third mixer 718 of signal 734 (Equation (13)) and signal 736 (Equation (14)) results in third mixer signal 738 defined by:

$$\begin{aligned} x_{q_2^c}(t) &= y_s^c(t) \times q_2^c(t) \\ &= A_s^c \sin(\omega t + \phi_s) \times \cos(\omega t + \phi_s - \Delta\phi_s) \\ &= \frac{A_s^c}{2} \sin(2\omega t + 2\phi_s - \Delta\phi_s) + \frac{A_s^c}{2} \sin(\Delta\phi_s) \end{aligned} \tag{15}$$

It can be seen there is a DC component and an AC component in (15). Suppose the AC component is filtered off using a second calibration filter 720 (e.g. low pass filter LPF5), only the DC component which is the error signal $V_e^s$ is left signal 740 given by $$V_e^s = \frac{A_s^c}{2}\sin(\Delta\phi_s) \quad (16)$$

The error signal $V_e^s$ is fed into control circuit 722 to adjust the second phase generator 522 until $V_e^s=0$ and the second phase generator 522 is tuned to generate the required annihilator signal 538 (FIG. 5) $\cos(\omega t+\phi_s)$, where $\phi_s$ is the phase of the wanted sample fluorescence signal 528.

The technique can also be used to tune first phase generator 512 to the fundamental phase $\phi_n$ where the output 724 of the second processor 706 (optical receiver 2), $y_g^n(t)$ is given by $$y_g^n(t) = A_0 + A_n^c \sin(\omega t + \phi_n) + \sum_{k=2}^{\infty} \alpha_k \sin(k\omega t + \phi_k) \quad (17)$$

The coefficients $\alpha_k$ and the phases $\phi_k$ for k=2, ..., ∞ of the signal 724 $y_g^n(t)$ can be unknown because mixing (10) with components of $y_g^n(t)$ in (17) results in $$\alpha_k \sin(k\omega t + \phi_k)\cos(\omega t + \phi_n - \Delta\phi_n) = \quad (18)$$
$$\frac{\alpha_k}{2}[\sin((k+1)\omega t + \phi_k + \phi_n - \Delta\phi_n) + \sin((k-1)\omega t + \phi_k - \phi_n + \Delta\phi_n)]$$

The resultant signal in (18) and $A_0 \cos(\omega t+\phi_n-\Delta\phi_n)$ can be filtered out using the same calibration filter 712 (LPF4). Therefore, the first phase generator 512 can be tuned to the fundamental phase $\phi_n$ of the signal $y_g^n(t)$ using the circuit 714.

Similarly, the output 734 of the third processor 716 (optical receiver 3) $y_g^s(t)$ can be given by $$y_g^s(t) = A_0 + A_s^c \sin(\omega t + \phi_s) + \sum_{k=2}^{\infty} \alpha_k \sin(k\omega t + \phi_k) \quad (19)$$

The coefficients $\alpha_k$ and the phases $\phi_k$ for k=2, ..., ∞ of the signal 734 $y_g^s(t)$ can be unknown. It follows that the second phase generator 522 can be tuned to generate the required annihilator signal 736 $\cos(\omega t+\phi_s)$ where $\phi_s$ is the fundamental phase of the signal 734 $y_g^s(t)$ using the control circuit 722.

Figure 8:
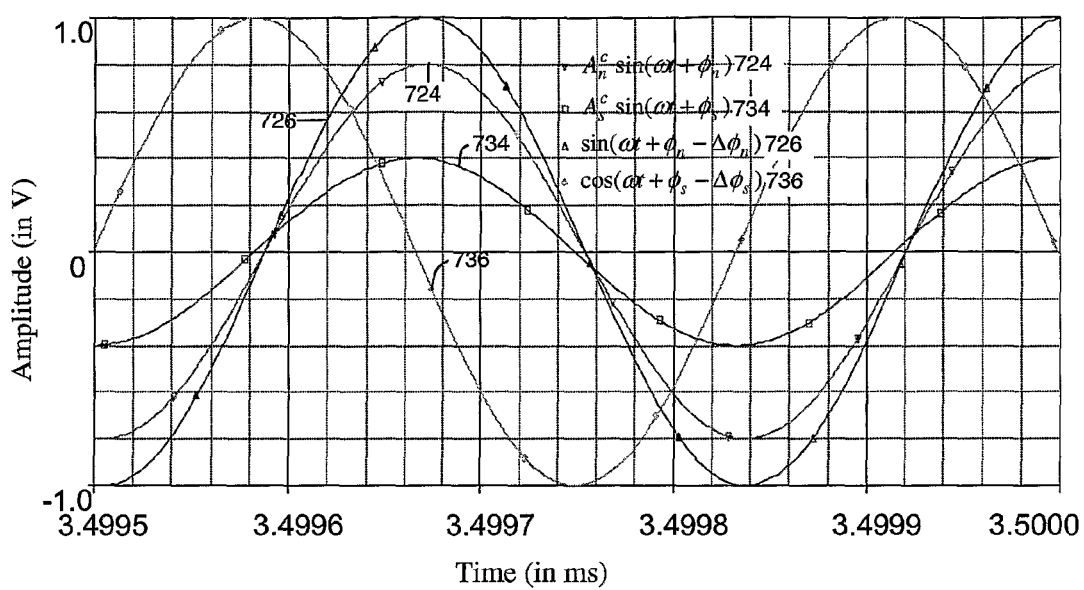
FIG. 8 is a graph illustrating the voltage-time curves for signals of the calibration circuit of FIG. 7.

With $A_n^c=0.8$ V and $A_s^c=0.4$ V, FIG. 8 shows voltage-time characteristics for electrical signals 724, 726, 734, 736 and that the calibration circuits are able to tune the first phase generator 512 to $\phi_n$ and the second phase generator 518 to generate the required annihilator signal 538 $\cos(\omega t+\phi_s)$ as the error signals at steady state for both calibration loops are zero.

Some non-exhaustive variations on the foregoing examples are now described.

Figure 9:
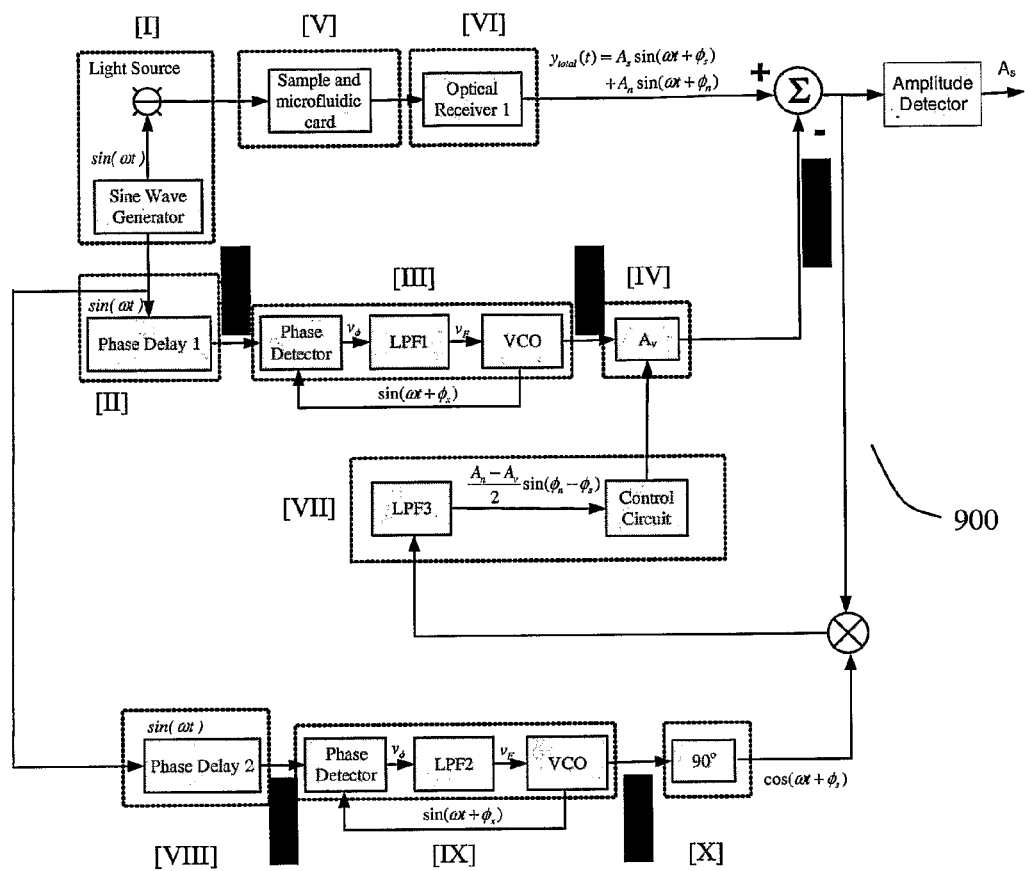
FIG. 9 is a block diagram illustrating an architecture for a fluorescence noise cancellation system using an additional two phase-locked loops and a quadrature phase shifter.

FIG. 9 illustrates the architecture of a fluorescence noise cancellation system using an additional two phase-locked loops and a quadrature phase shifter. This system architecture 900 comprises ten main blocks as follows: the tuneable modulated light source system [I], the phase delay generator 1 [II], the phase-locked loop circuitry 1 [III], the variable gain $A_v$ [IV], the sample (analyte and microfluidic card) [V], the optical receiver 1 [VI], the control circuit [VII], the phase delay generator 2 [VIII], the phase-locked loop circuitry 2 [IX], and the quadrature phase shifter [X].

Figure 10:
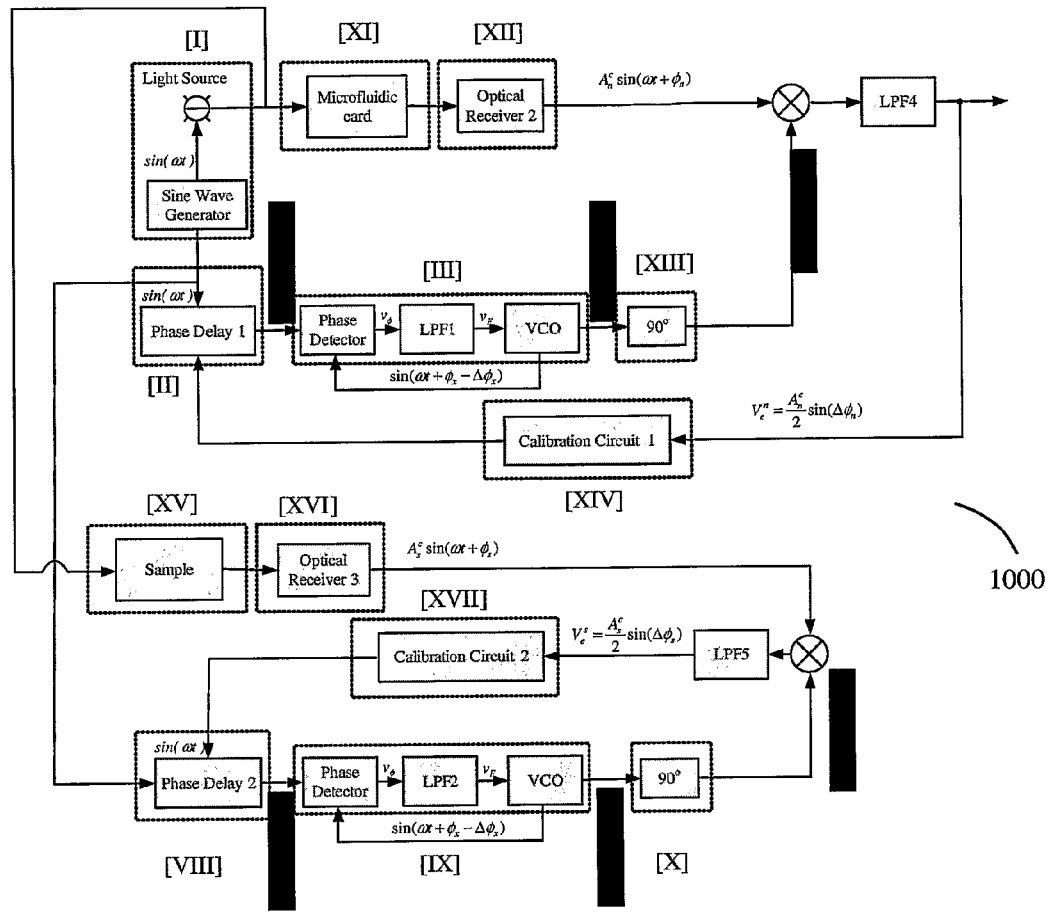
FIG. 10 is a block diagram illustrating an architecture for a calibration circuit for the circuit of FIG. 9.

The calibration of the circuit of FIG. 9 is described with reference to the circuit architecture 1000 of FIG. 10. The calibration of the phase delay generators requires an additional seven blocks namely the microfluidic card [XI], the optical receiver 2 [XII], the quadrature phase shifter [XIII], the calibration circuit 1 [XIV], the sample [XV], the optical receiver 3 [XVI], and the calibration circuit 2 [XVII].

Figure 11:
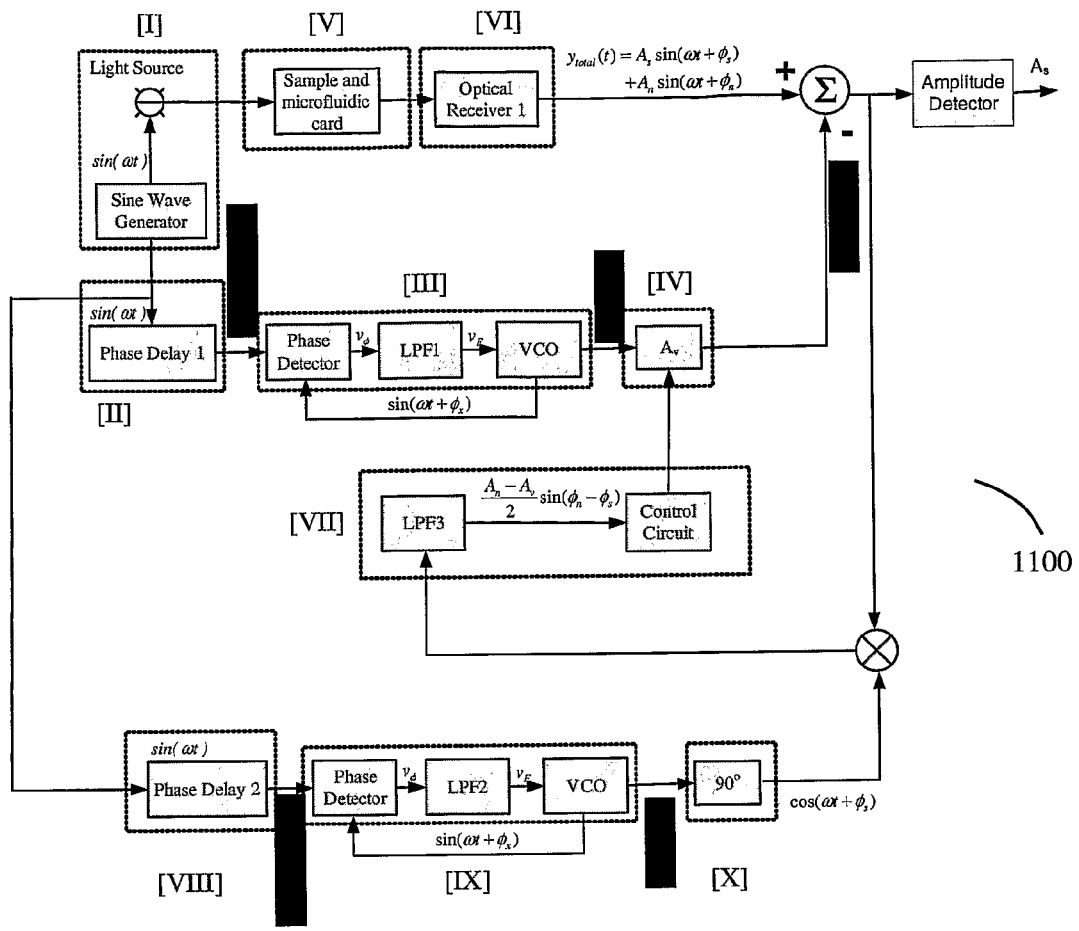
FIG. 11 is a block diagram illustrating an architecture for a fluorescence noise cancellation system which uses an additional two alternative phase-locked loops and a quadrature phase shifter

FIG. 11 illustrates another alternative architecture for a fluorescence noise cancellation system which uses an additional two alternative phase-locked loops and a quadrature phase shifter. This is illustrated as architecture 1100.

Figure 12:
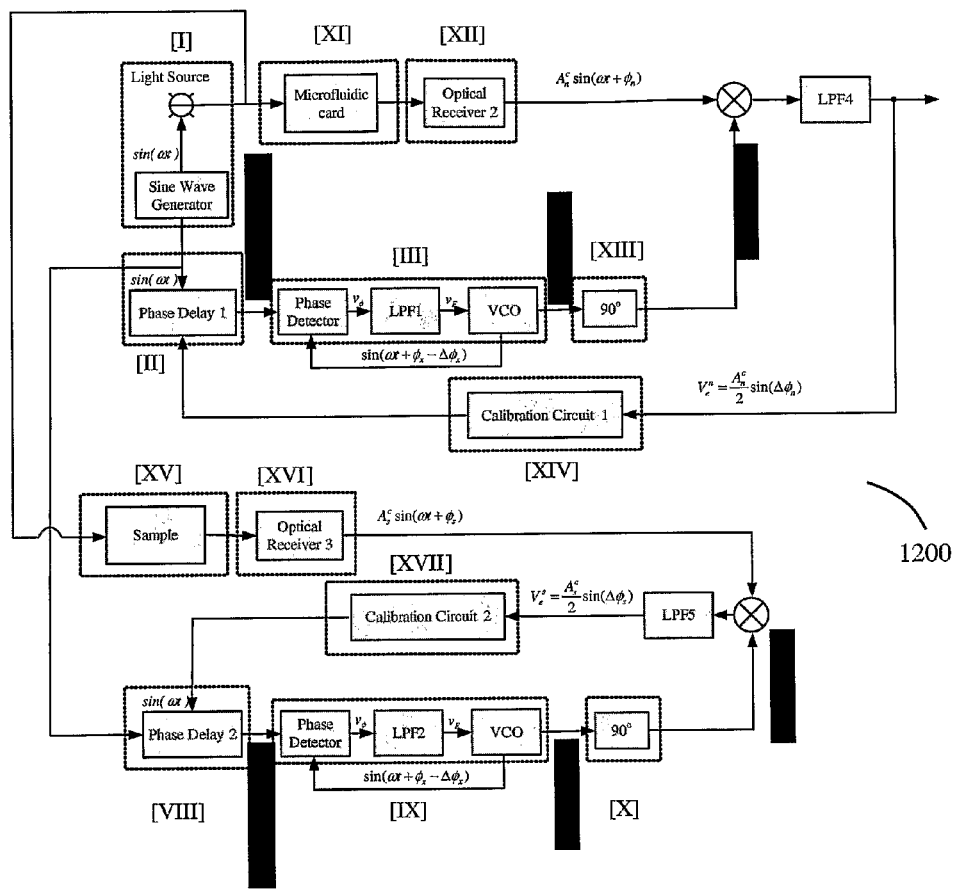
FIG. 12 is a block diagram illustrating an architecture for a calibration circuit for the circuit of FIG. 11.

The circuit 1100 of FIG. 11 is calibrated according to the calibration circuit 1200 of FIG. 12.

Figure 13:
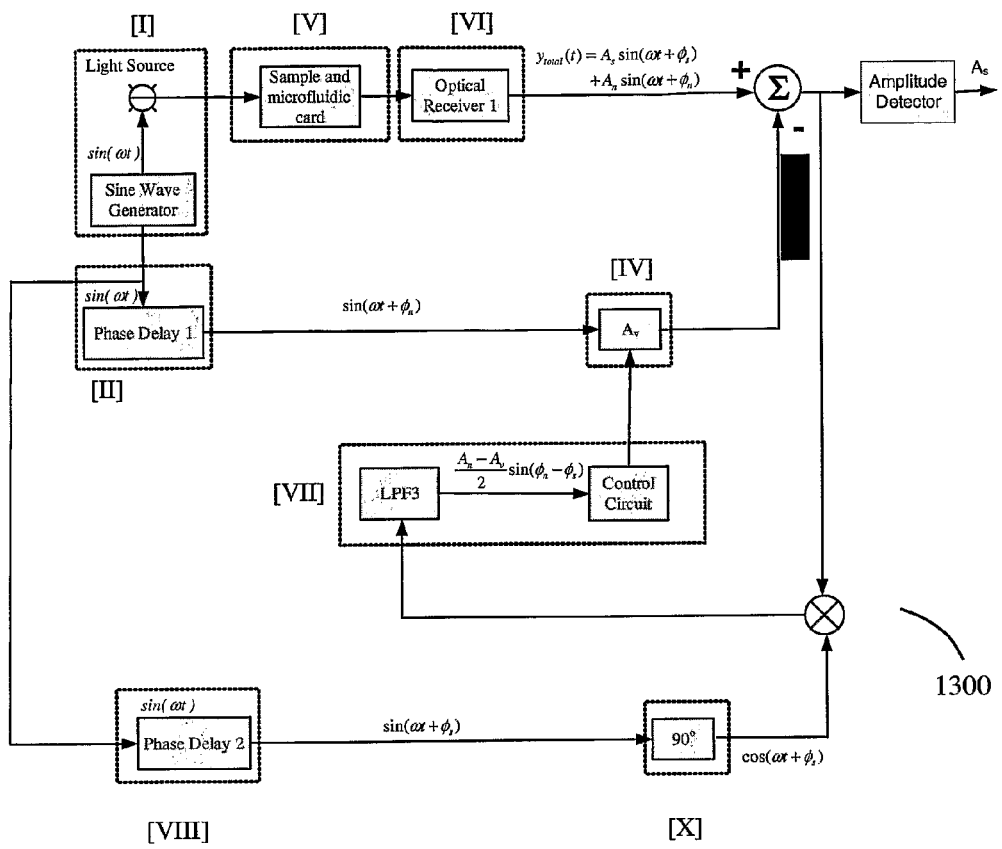
FIG. 13 is further alternative circuit for analysing the fluorescent sample.
Figure 14:
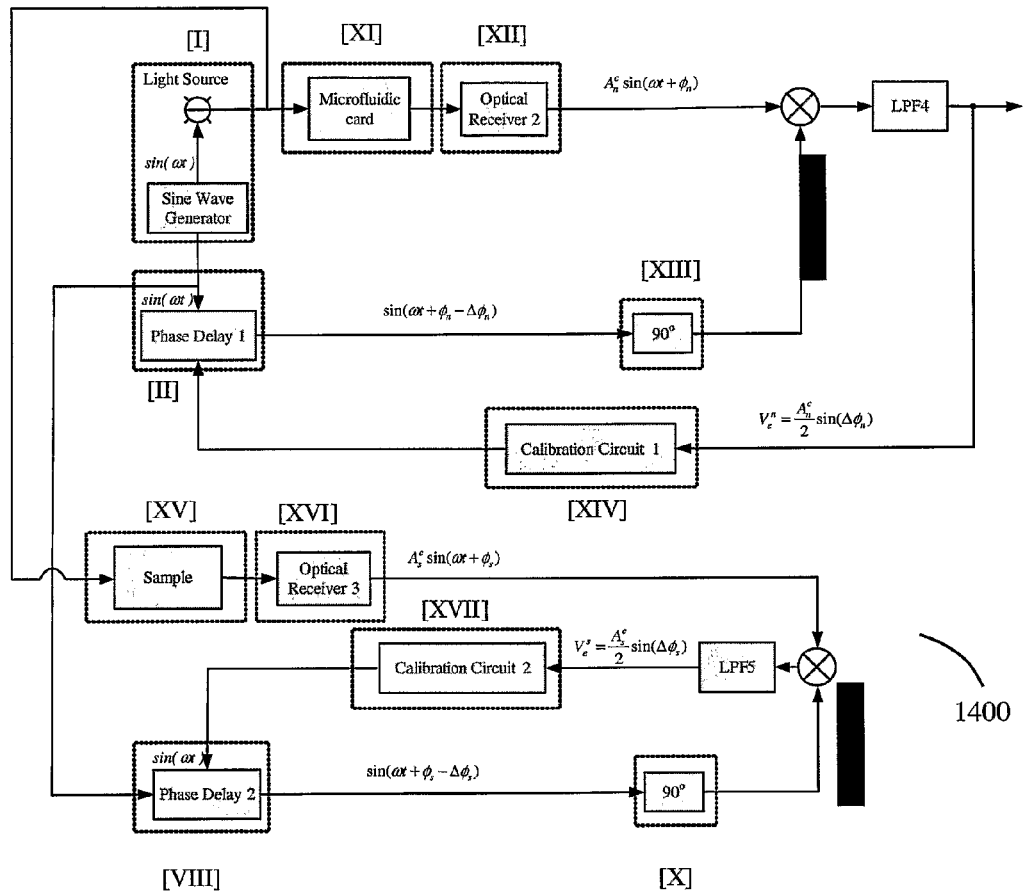
FIG. 14 is a block diagram illustrating an architecture for a calibration circuit for the circuit of FIG. 13.

A further alternative circuit 1300 for analysing the fluorescent sample is illustrated in FIG. 13. The circuit 1300 uses an additional quadrature phase shifter. FIG. 14 illustrates a circuit architecture 1400 for calibrating the circuit 1300 of FIG. 13.

Figure 15:
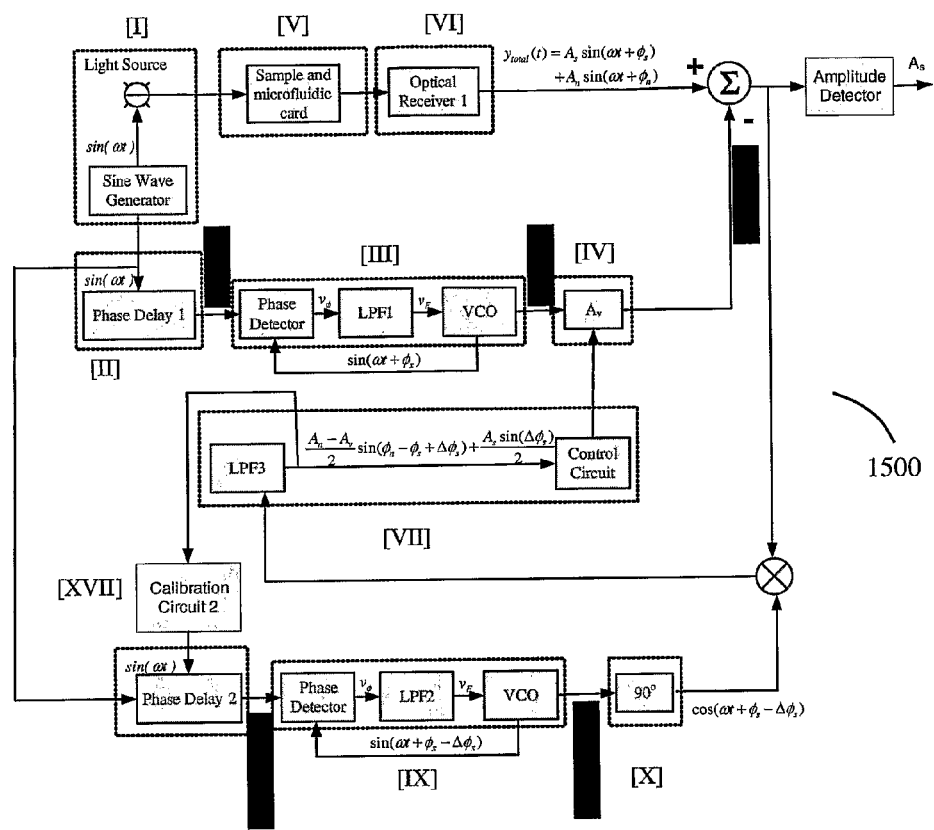
FIG. 15 is a block diagram illustrating the layout of the modified fluorescence noise cancellation system using two additional phase-lock loops and a quadrature phase shifter.

The layout of the modified fluorescence noise cancellation system using two additional phase-lock loops and a quadrature phase shifter is illustrated in FIG. 15 In this and the following figures, the error variable is a sum of the error signals of the control circuit and calibration circuit 2 given by FIGS. 5, and 7. The error variable is fed into the control circuit and calibration circuit 2. The calibration circuit 2 and control circuit will be more difficult to design due to the interactions between the control loop and calibration loop 2.

Figure 16:
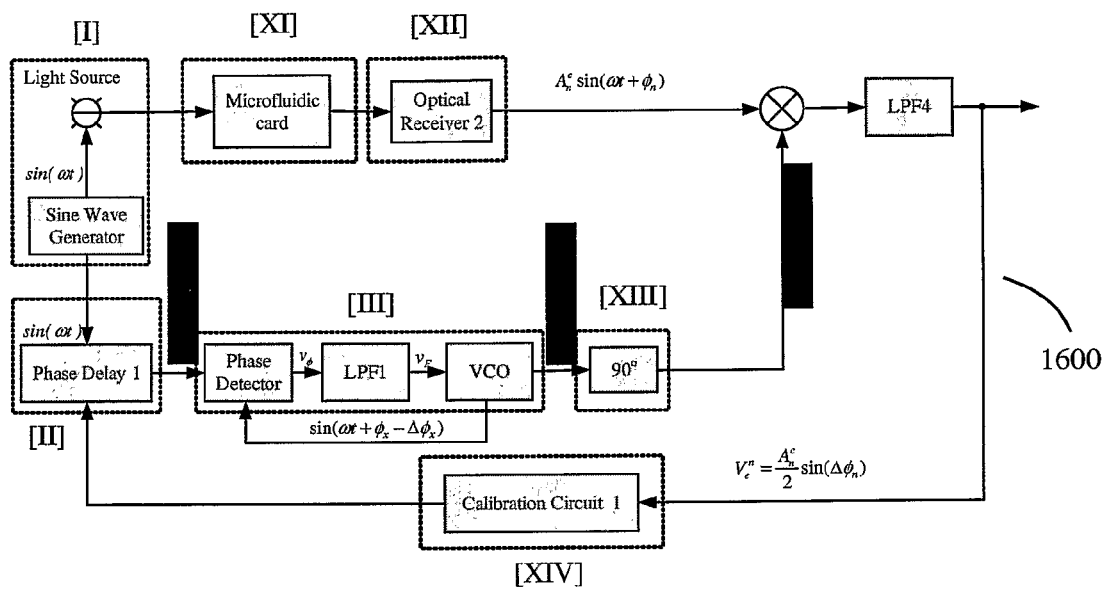
FIG. 16 is a block diagram illustrating the layout of the calibration circuit of the modified fluorescence noise cancellation system with additional phase lock loop.

An alternative calibration circuit 1600 is illustrated in FIG. 16. This circuit is a modified fluorescence noise cancellation system with an additional phase-locked loop.

Figure 17:
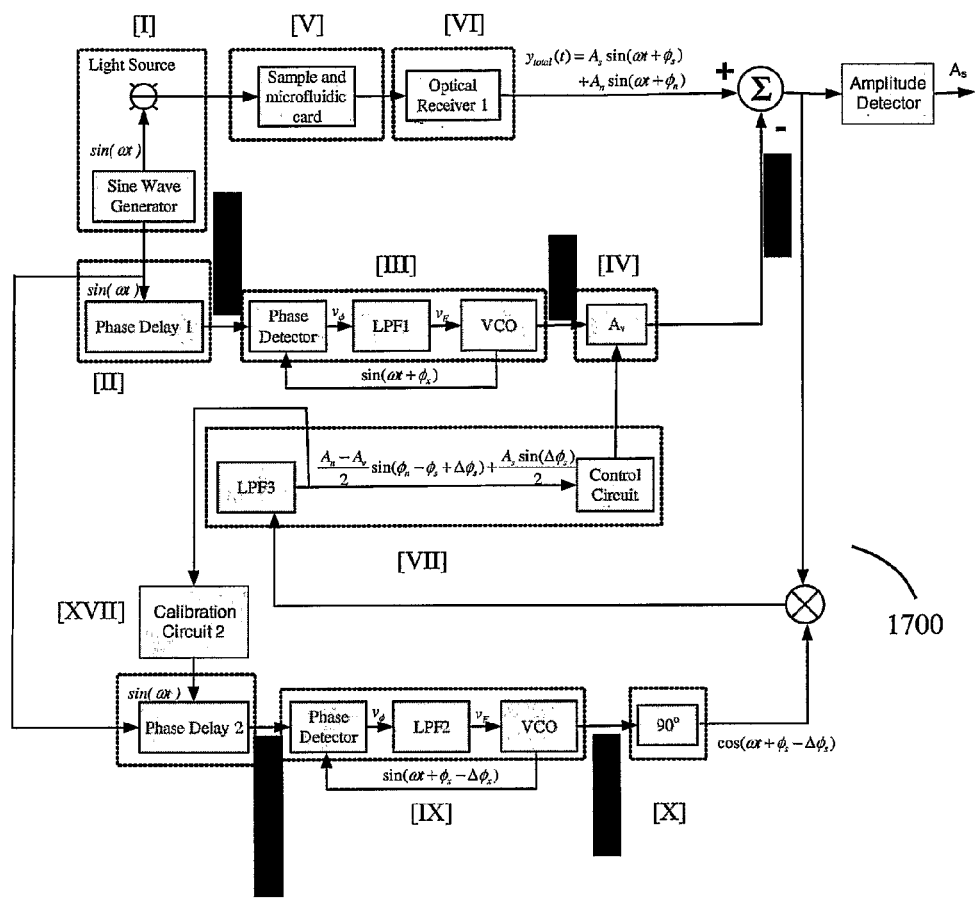
FIG. 17 illustrates another alternative circuit 1700 which provides a modified fluorescence noise cancellation system using an additional two alternative phase-locked loops and a quadrature phase shifter.

FIG. 17 illustrates another alternative circuit 1700 which provides a modified fluorescence noise cancellation system using an additional two alternative phase-locked loops and a quadrature phase shifter.

Figure 18:
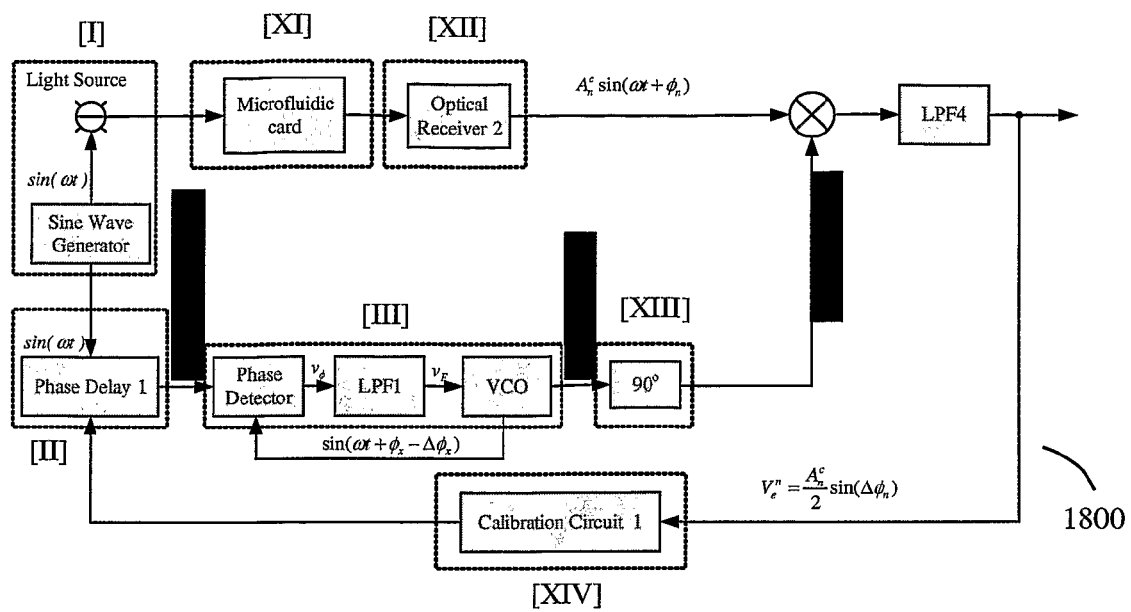
FIG. 18 is illustrates the layout of another calibration circuit 1800 using an additional alternative phase-locked loop.

FIG. 18 illustrates the layout of another calibration circuit 1800 using an additional alternative phase-locked loop.

Figure 19:
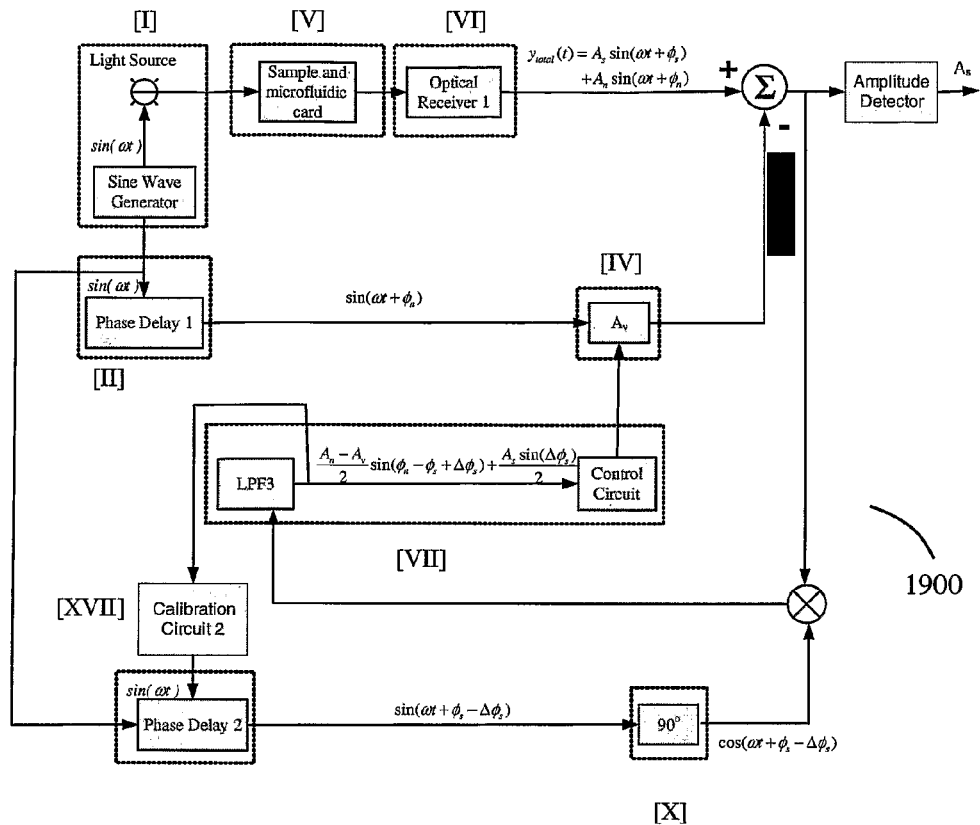
FIG. 19 illustrates another circuit 1900 for a noise cancellation system using a quadrature phase shifter.

FIG. 19 illustrates another circuit 1900 for a noise cancellation system using a quadrature phase shifter.

Figure 20:
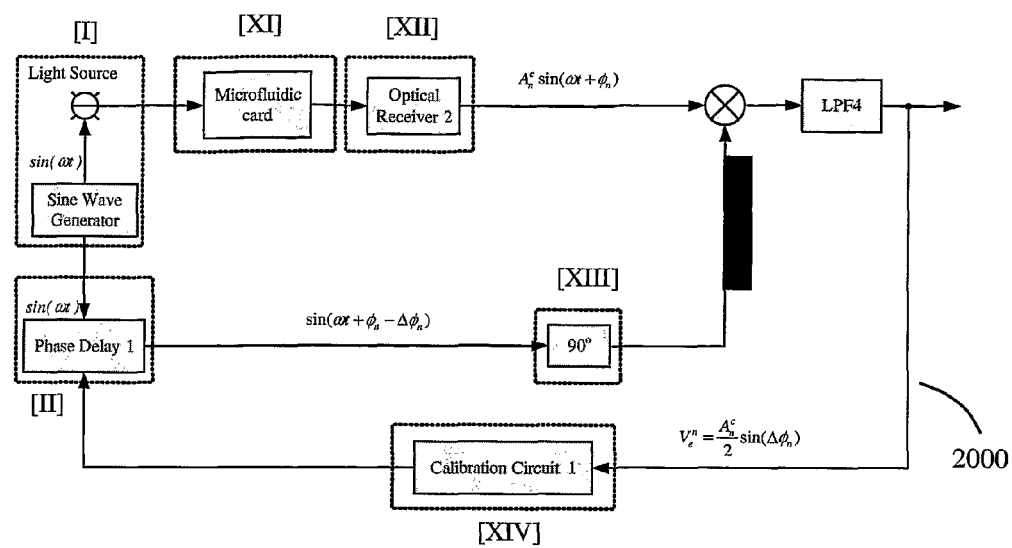
FIG. 20 illustrates a calibration circuit 2000 which defines a modified fluorescence noise cancellation system.

FIG. 20 illustrates a calibration circuit 2000 which defines a modified fluorescence noise cancellation system.

Figure 21:
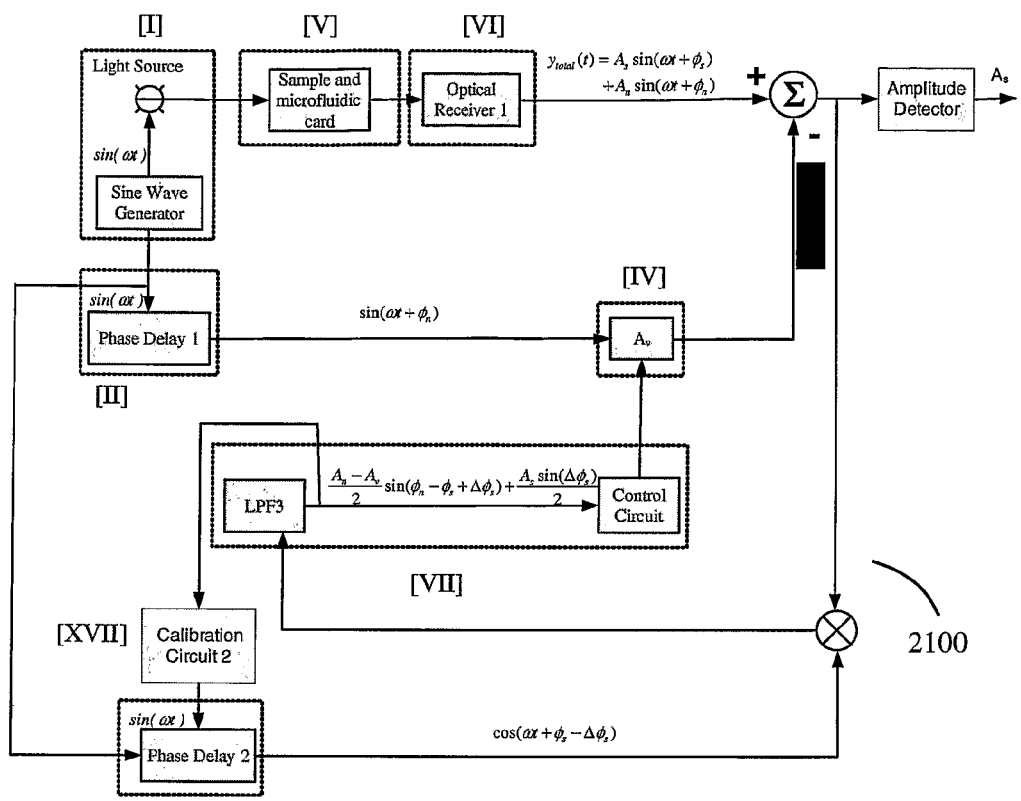
FIG. 21 illustrates an alternative circuit 2100 which defines another modified fluorescence noise cancellation system.

FIG. 21 illustrates an alternative circuit 2100 which defines another modified fluorescence noise cancellation system.

It will be appreciated the invention has been described by way of example only and various modifications may be made to the detail of implementation without departure from the spirit and scope of the appended claims.

The invention claimed is:

1. An apparatus for analyzing a fluorescent sample disposed on a substrate, the apparatus comprising:
   a first processor for producing a first electrical signal derived from a first light signal component from the sample and a second electrical signal derived from a second light signal component from the substrate, wherein the apparatus is arranged to produce the first and second electrical signals such that there is a phase difference between phases of the first and second electrical signals; and
   a control circuit for producing an attenuation signal for attenuating the second signal, wherein the control circuit comprises a first phase generator and a variable gain module, the first phase generator being arranged to set a phase of the attenuation signal and the variable gain module being arranged to set an amplitude of the attenuation signal, the control circuit being arranged for the attenuation signal to cancel or cancel substantially the second electrical signal.

2. Apparatus according to claim 1, wherein the first phase generator is arranged to set the phase of the attenuation signal to be equal or substantially equal to the phase of the second electrical signal.

3. Apparatus according to claim 1, wherein the variable gain module is arranged to set the amplitude of the attenuation signal to be equal or substantially equal to the amplitude of the second electrical signal.

4. Apparatus according to claim 1, wherein the control circuit comprises a summer module, the summer module being arranged to attenuate the second electrical signal by subtracting the attenuation signal from the second electrical signal.

5. Apparatus according to claim 4, wherein the control circuit is arranged for an output of the summer module to be fed back for control of the variable gain module.

6. Apparatus according to claim 5, wherein the control circuit comprises a second phase generator arranged to provide an output signal to be mixed by a first mixer with the output of the summer module to produce a first mixed signal for control of the variable gain module.

7. Apparatus according to claim 6, wherein the second phase generator is arranged to set its output signal to have a phase equal to or substantially equal to a phase of the first electrical signal.

8. Apparatus according to claim 1, wherein the apparatus comprises a first calibration circuit for calibrating the first phase generator, the first calibration circuit comprising a second processor for producing a third electrical signal derived from the second light signal component from the substrate, wherein the apparatus is arranged to produce the third electrical signal without the third electrical signal containing a component derived from the first light signal component.

9. Apparatus according to claim 8, wherein the first calibration circuit comprises:
a quadrature phase shifter arranged to shift a phase of an output signal of the first phase generator to produce a shifted signal, the shifted signal to be mixed with the third electrical signal by a second mixer to produce a second mixed signal; and
a first calibration filter for filtering the second mixed signal, an output of the first calibration filter being arranged to be fed back as a control input of the first calibration circuit.

10. Apparatus according to claim 6, wherein the apparatus comprises a second calibration circuit for calibrating the second phase generator, the second calibration circuit comprising a third processor for producing a fourth electrical signal derived from the first light signal component from the substrate, wherein the apparatus is arranged for the third processor to produce the fourth electrical signal without the fourth electrical signal containing a component derived from the second light signal component.

11. Apparatus according to claim 10, wherein the second calibration circuit comprises a third mixer for mixing the fourth electrical signal with an output of the second phase generator to produce a third mixed signal and a second calibration filter for filtering the third mixed signal to be fed back as a control input of the second calibration circuit.

12. An apparatus for analysing a fluorescent sample disposed on a substrate, the apparatus comprising:
a tuneable modulated light source for exciting the fluorescent sample;
an optical receiver for receiving light signal components from the fluorescent sample and from the substrate;
a first phase delay generator and a variable gain module;
a second phase delay generator; and
a control circuit for the variable gain module.

13. A method of analysing a fluorescent sample disposed on a substrate, the method comprising:
producing a first electrical signal derived from a first light signal component from the sample and a second electrical signal derived from a second light signal component from the substrate;
producing the first and second electrical signals such that there is a phase difference between phases of the first and second electrical signals;
producing an attenuation signal for attenuating the second electrical signal; and
setting a phase of the attenuation signal and setting an amplitude of the attenuation signal such that the attenuation signal cancels or cancels substantially the second electrical signal.

14. A method of analysing a fluorescent sample disposed on a substrate, the method comprising:
tuning a tuneable modulated light source to excite the fluorescent sample;
receiving light signal components from the fluorescent sample and from the substrate and producing respective first and second electrical signals; and
controlling a first phase delay generator and a variable gain module and a second phase delay generator to produce an attenuation circuit to attenuate the second electrical signal.

15. A method of analysing a fluorescent sample disposed on a substrate using the apparatus of claim 1.

* * * * *